United States Patent

Hamilton

(10) Patent No.: US 6,738,723 B2
(45) Date of Patent: *May 18, 2004

(54) PHARMACY PILL COUNTING VISION SYSTEM

(75) Inventor: Rodney N. Hamilton, Gardner, KS (US)

(73) Assignee: Scriptpro LLC, Mission, KS (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/408,730

(22) Filed: Apr. 7, 2003

(65) Prior Publication Data

US 2003/0204357 A1 Oct. 30, 2003

Related U.S. Application Data

(63) Continuation of application No. 09/779,290, filed on Feb. 8, 2001, now Pat. No. 6,574,580.
(60) Provisional application No. 60/181,979, filed on Feb. 11, 2000.

(51) Int. Cl.[7] ............................................... G06F 19/00
(52) U.S. Cl. ............................ 702/128; 137/2; 382/128
(58) Field of Search ....................... 702/128, 81; 137/2; 221/129, 219

(56) References Cited

U.S. PATENT DOCUMENTS

| 3,069,654 A | 12/1962 | Hough |
| 5,337,919 A | 8/1994 | Spaulding et al. ............. 221/2 |
| 5,713,487 A | 2/1998 | Coughlin ........................ 221/2 |
| 5,762,235 A | 6/1998 | Coughlin ........................ 221/6 |
| 5,798,020 A | 8/1998 | Coughlin et al. ............ 156/542 |
| 5,860,563 A | 1/1999 | Guerra et al. ................ 221/172 |
| 5,873,488 A | 2/1999 | Guerra ........................ 221/220 |
| 5,897,024 A | 4/1999 | Coughlin et al. ........... 221/135 |
| 6,085,938 A | 7/2000 | Coughlin .................... 221/203 |
| 6,155,485 A | 12/2000 | Coughlin et al. ........... 235/383 |
| 6,161,721 A | 12/2000 | Kudera et al. .................. 221/9 |
| 6,206,590 B1 | 3/2001 | Thomas et al. ............. 400/586 |
| 6,318,630 B1 | 11/2001 | Coughlin et al. ........... 235/375 |
| 6,343,711 B1 | 2/2002 | Coughlin .................... 221/217 |
| 6,421,584 B1 | 7/2002 | Norberg et al. ............. 700/242 |
| 6,574,580 B2 * | 6/2003 | Hamilton .................... 702/128 |
| 6,578,734 B1 | 6/2003 | Coughlin .................... 221/219 |
| 6,592,005 B1 | 7/2003 | Coughlin et al. ........... 221/129 |

* cited by examiner

*Primary Examiner*—Kamini Shah
(74) *Attorney, Agent, or Firm*—Hovey Williams LLP

(57) ABSTRACT

A semi-automated pill counting system (10) using digital imaging technology and image recognition software including a modified Hough Transform. The system (10) comprises a light source (12); a modified pharmacist's tray (14); a digital camera (16); and a personal computer (PC) (18), with the PC (18) storing and executing the image recognition software. A roughly estimated number of pills are placed upon the tray (16) and illuminated by the light source (12), whereafter a digital image of the pills is produced by the camera (16) and sent via an interface to the PC (18). The image recognition software counts the pills present in the image and displays a count result. Based upon the count result, the pharmacist adds or removes pills to the tray (14), as appropriate, to complete the process.

17 Claims, 2 Drawing Sheets

PHARMACY PILL COUNTING VISION SYSTEM

RELATED APPLICATIONS

The present application relates to and claims priority with regard to all common subject matter of provisional patent application titled "Computer Interfaced Camera For Counting Drug Units Such As Pills", Serial No. 60/181,979, filed Feb. 11, 2000. The identified provisional patent application is hereby incorporated into the present application by reference. Further, the present application is a continuation of non-provisional patent application entitled "Pharmacy Pill Counting Vision System," Ser. No. 09/779,290, filed Feb. 8, 2001, and is hereby incorporated into the present application by reference.

COMPUTER PROGRAM LISTING APPENDIX

A computer program listing appendix containing the source code of a computer program that may be used with the present invention is incorporated herein by reference from non-provisional patent application entitled "Pharmacy Pill Counting Vision System," Ser. No. 09/779,290, filed Feb. 8, 2001. The source code incorporated by reference is listed as follows:

| Filename: | Date of Creation: | Size (Bytes): |
|---|---|---|
| COLORL~1.CPP | Jan. 26, 2001 | 7,307 |
| IMAGEA~1.CPP | Jan. 26, 2001 | 17,568 |
| PCA_DLG.CPP | Jan. 26, 2001 | 20,654 |
| PERIME~1.CPP | Jan. 26, 2001 | 17,797 |
| PERIME~2.CPP | Jan. 26, 2001 | 30,714 |
| PILLLIST.CPP | Jan. 26, 2001 | 61,258 |

BACKGROUND OF THE INVENTION

1. Field of the Invention

The present invention relates to automated and semi-automated pill counting systems. More particularly, the invention relates to a semi-automated pill counting system using digital imaging technology and image recognition software.

2. Description of the Prior Art

Prescriptions are being issued at an ever-increasing rate due to a number of factors, including managed care's focus on prescriptions as an alternative to inpatient care; an aging population; and increased consumer knowledge due, in large part, to direct-to-consumer advertising. Dispensed prescriptions are projected to reach three billion in 2001 and jump to four billion annually by 2004, with only a six percent increase in the number of graduating pharmacists over the same time period. As prescription volume and workload increases, the potential for error by overworked pharmacists increases as well, which has the undesirable effect of reducing patient confidence and overall safety. Furthermore, given the number of prescriptions dispensed and the average cost of each pill, even small error rates can result in large financial losses to both the pharmacist and the consumer.

Traditional manual pill counting methods involve pouring a roughly estimated quantity of pills onto a tray; sliding the pills from a first side of the tray to a second side in small, easily countable groups; and repeating until a desired pill count is reached, whereupon the pills are bottled and labeled for dispensation. As will be appreciated by those in the pharmacological arts, though suited for small pill counts or low numbers of prescriptions, these traditional methods are inefficiently time consuming for large pill counts or high volume dispensing.

Another drawback of time-consuming manual pill counting is that the more time a pharmacist spends counting pills, the less time he or she has available for direct patient contact and care, including educating the patient about the prescribed medicine. This is particularly unappealing to pharmacists who are unsatisfied counting pills after years of schooling and training, and would much prefer more meaningful direct interaction with their customers.

Sophisticated and efficient fully automated pill counting systems exist that are able to handle the mundane, repetitive counting function without significant error while freeing the pharmacist for more stimulating and rewarding activities. The SP200 system, manufactured and sold by ScriptPro LLC, for example, can dispense sixty or more prescriptions per hour, potentially freeing four or more pharmacists from full time counting duties. Furthermore, patient wait times are reduced even as their wait is made more productive by increased direct contact with their pharmacist.

Unfortunately, fully automated pill counting systems are typically not cost-effective for small pharmacies, so a need has arisen for smaller, semi-automated pill counting apparatuses. Such apparatuses use a variety of counting technologies. One existing technology, for example, first weighs a group of pills and then determines their number based upon an average pill weight. Unfortunately, this relatively primitive method is unacceptably error prone due to factors such as incorrect average pill weights, weight-altering residue on the scales or equipment, incorrect calibration, and pill manufacturing changes that affect pill weight. Furthermore, accurate dosing of a pill's active ingredient does not necessarily translate into consistent combined active and inactive ingredient weight from pill to pill.

Another existing technology couples a light beam and a simple photosensor with a counter such that when a falling or moving pill breaks the light beam the counter is incremented. Unfortunately, these unsophisticated systems are typically unable to discriminate between broken pill fragments and whole pills, or close clusters of two or three pills that break the light beam overlappingly or almost simultaneously.

Due to the above-described and other problems in the art of automated pill counting, a need exists for an improved pill counting technology and apparatus.

SUMMARY OF THE INVENTION

The present invention solves the above-described and other problems and provides a distinct advance in the art of pill counting. More specifically, the present invention is a semi-automated pill counting system using digital imaging technology and image recognition software to facilitate more efficient, accurate, and cost-effective pill counting, thereby freeing the pharmacist from this mundane task to engage in more meaningful and direct customer interactions.

The preferred system comprises a light source; a modified pharmacist's tray; a digital camera; and a personal computer (PC), with the PC storing and executing image recognition software. The light source provides light of a sufficient quality and intensity to ensure accurate counts. The camera is a conventional digital camera securely mounted over a work surface and coupled with the PC via an interface. The pharmacist's tray provides an area upon which uncounted pills may be placed for viewing by the camera. The work surface includes features ensuring that the tray is consistently centered. The PC is a conventional personal computer with sufficient computing resources to store and execute the image recognition software. The PC also provides a user interface with the counting software. In another embodiment, depending upon design and application requirements, the image recognition software is stored and executed on dedicated hardware or firmware, which allows for a unitized or portable device. The preferred image recognition software is based upon a modified Hough Transform technique.

For example, given a prescription for eighty pills, a pharmacist first pours onto the tray a number of pills estimated to be sufficient to fill the prescription. Using the traditional pill counting method, the pharmacist would then manually count out eight groups of ten or sixteen groups of five. Using the present system, however, the pharmacist merely causes the digital camera to produce a digital image of the actual number of pills on the tray, whereupon the image is sent via the interface to the PC. The image recognition software executed by the PC counts the pills in the image; determines the number of pills, if any, that must be added or removed to arrive at the prescribed amount; and communicates that number to the pharmacist. For example, if eighty-seven pills are counted, the software instructs the pharmacist that seven pills should be removed and then verifies that the correct number remain. Thus, using the present invention, the pharmacist need perform only two steps rather than eight or sixteen or more. Less time is spent counting pills and more time is spent interacting with the customer. Furthermore, fewer counting errors are made, thereby reducing health risks and financial losses.

These and other novel features of the present invention are described in more detail in the section titled DETAILED DESCRIPTION OF A PREFERRED EMBODIMENT, below.

BRIEF DESCRIPTION OF THE DRAWING FIGURES

The present invention is described in detail below with reference to the attached drawing figures, wherein.

DETAILED DESCRIPTION OF A PREFERRED EMBODIMENT

Figure 1:
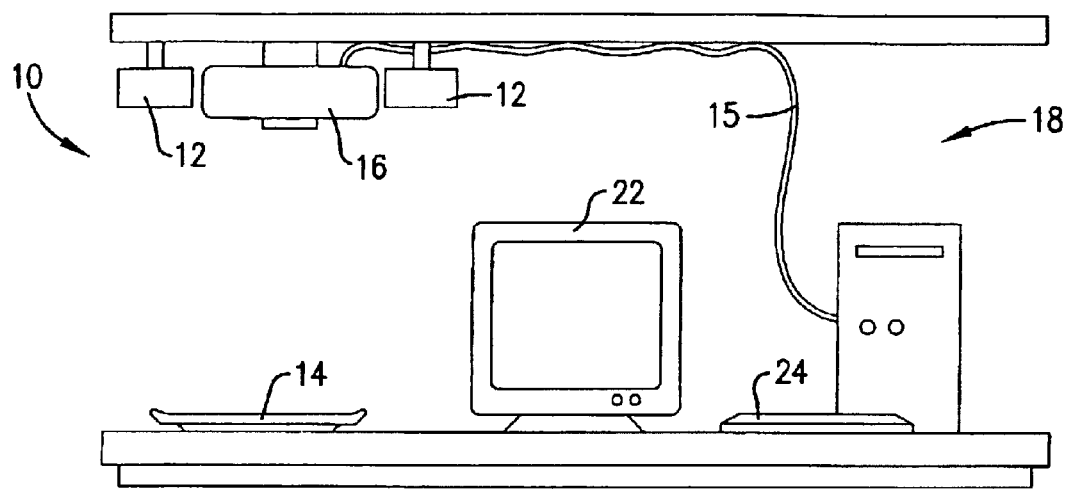
FIG. 1 is an isometric view of a preferred system for implementing the present invention.

Referring to FIG. 1 a semi-automated pill counting system 10 is shown constructed in accordance with a preferred embodiment of the present invention and operable to facilitate more efficient and accurate pill counting. The preferred system 10 broadly comprises a light source 12; a modified pharmacist's tray 14; a digital camera 16; and a personal computer (PC) 18, with the PC 18 storing and executing image recognition software.

The light source 12 provides for an evenly and well lit work surface using light of at least the minimum quality and brightness required by the digital camera 16 and image recognition software to achieve accurate pill counts. Thus, though the present invention is independent of any particular type or brand of light or bulb, a minimum degree of light quality and brightness will be necessary and desirable depending upon the performance characteristics of other system components. Preferably, the lighting 12 is located approximately eighteen inches above the work surface, which is a compromise between good lighting and an open, useable work surface.

The modified pharmacist's tray 14 is operable to contain a number of pills within the camera's field of view. The preferred tray 14 has an anti-reflective surface to avoid image interference; has clearly defined and distinct first and second portions 30,32 for uncounted and excess pills, respectively, with only the first portion 30, being approximately 8×6 inches, viewable by the camera 16; and is easy to clean so as to prevent contamination of prescriptions. The first and second tray portions 30,32 may be defined and separated by a visual or physical divider 34, such as a line or raised ridge. Furthermore, it is preferable that the first tray portion 30 have a changeable background color, possible accomplished with colored inserts, so as to allow for improved color contrast where colored pills are being counted. It may also be desirable to provide a mechanism, such as a small motor, whereby the tray 14 can be vibrated to ensure even, single-layer distribution of the pills to be counted.

The digital camera 16 is a high quality conventional digital camera coupled with the PC 18 via an interface 15 and operable to capture and digitize images for use by the PC 18. The present system 10 is independent of any particular type or brand of digital camera, and a variety of cameras are available, each having different performance characteristics, including speed, color accuracy, and resolution, that may effect overall performance of the system 10. With the exception of some multi-pass cameras, most are of comparable exposure speed. The PC interface 15 plays a much larger role in camera and system speed, with, for example, an RS-232 interface providing a transfer rate of 115.2 kbits/sec and a SCSI interface providing a transfer rate of 80,000 kbits/sec. Suitable available interfaces include Ethernet, Firewire, and USB.

Color accuracy of the camera 16 is important for algorithms performing comparisons with a master image. Furthermore, the counting accuracy of some such algorithms is negatively affected by even small variances in image color quality.

Minimum resolution of the camera 16, measured in "pixels-per-square-inch", is limited by such factors as minimum pill size, lack of distinct pill features, and algorithm requirements. Higher resolution, though perhaps more accurate, may slow the process, though a faster PC or processor may compensate. For example, there is four times as much data in a 640×480 pixel image than in a 320×240 pixel image. Ultimately, camera speed, interface type, color accuracy, and resolution choices are all matters of design tradeoff, with better performance typically translating into higher cost.

A suitable and preferred camera 16 is Polaroid's Digital Microscope Camera le, having a maximum resolution of 1600×1200 pixels, which, when combined with the preferred 8×6 inch counting area, yields an image with 40,000 pixels-per-square-inch resolution. An alternate 800×600 resolution can be used (10,000 pixels-per-square-inch) for larger pills to reduce processing time. The camera 16 is preferably positioned approximately eighteen inches above the work surface, which is a compromise between good viewing and an open, useable work area.

The PC 18 may be any conventional computing device, such as a commonly available personal computer, with sufficient computing resources to store and execute the image recognition software and display count results. Peripheral equipment resources preferably include a display 22, such as a monitor, and one or more input devices 24, such as a keyboard, keypad, or mouse. A suitable and preferred computer utilizes at least a Pentium II 400 MHz processor, and is available, for example, from Micron Electronics Incorporated, Dell Computer Corporation, and Compaq Computer Corporation. Again, the exact physical and performance characteristics of the PC 18, like other system components, are matters of design, application, and the requirements of other components. The well-known tradeoff of performance versus cost arises here as well, with faster processing speeds typically costing more. For example, a very high resolution image will typically require a longer processing time, though this can be offset by a faster processing speed.

In another embodiment, depending upon design and application requirements, the PC 18 is eliminated and the image recognition software is stored and executed on dedicated hardware or firmware coupled with an input device, such as a keypad, and a display. This adaptation offers the advantage of smaller, lighter components and is particularly desirable, for example, in unitized or portable embodiments of the present invention. The processor may be any suitable device or circuit operable to receive the digital image, execute the image recognition software, and generate a count result. The display may be any suitable display, such as a light emitting diode (LED) display of liquid crystal display (LCD), for communicating the count result.

The image recognition software comprises a combination of program code segments operable to receive the digitized image from the digital camera 16, accurately count the number of pills present in the image, and communicate the count to an operator via the PC 18 or other display. A preferred embodiment of the image recognition software, suitable for use with the above described system and the below described method in implementing and practicing the present invention, is appended hereto as a computer listing appendix. The software may be stored on any computer readable memory media, including magnetic or optical, forming a part of the PC 18, such as a hard disk drive, or otherwise accessible thereto, such as a floppy disk or CD-ROM. Furthermore, the software may be written in any suitable programming language executable by the PC 18, including Assembly, C++, or Java.

Several types of image recognition algorithms are well-known, ranging from counting pixels to comparing permutations of scaled and rotated regions. A sufficiently complex algorithm, for example, exposed to an image of an unknown number of an unknown type of pill, could both count the pills and identify the pill type. Such complexity, however, comes at great costs, both in terms of cash outlay for the software and high-end supporting hardware, and overall system speed.

The nature of the present invention, however, lends itself to several assumptions that allow for a less complex image recognition algorithm. In particular, the controlled, professional pharmacy environment in which the system 10 is used allows one to assume, for example, that the work surface will be clean, evenly well lit, and contain only pills of a single type, and that the focal distance of the camera 16 will be fixed and consistent between applications.

A suitable and preferred algorithm is a variation of the Hough Transform wherein adjustments for scale have been omitted for the sake of processing speed. The Hough Transform is an image analysis tool developed by Paul Hough and subsequently disclosed in U.S. Pat. No. 3,069,654, issued in 1962, which is hereby incorporated by reference. The Hough Transform allows for recognition of global patterns in an image space by recognition of local patterns in a transformed parameter space. The transform technique can be used to isolate features of a particular shape within an image, and group collinear or almost collinear points into image structures. Because it requires that the desired features be specified in some parametric form, the classical Hough Transform is most commonly used for the detection of regular curves such as lines, circles, or ellipses, which makes it ideal for detecting the regular curves of pills.

An advantage of the Hough transform is that it is tolerant of low resolution effects, including missing or contaminated data and, particularly, gaps in feature boundary descriptions or unsharp object boundaries. Another advantage is that, with the aid of anti-aliasing techniques, it is relatively tolerant of image noise.

The above described system 10 and image recognition software may be more generally and broadly viewed as accomplishing a method of reliably and accurately counting pills with minimal operator involvement. As will be appreciated by those with skill in the art, however, the method may be implemented using any hardware, software, or firmware or combination thereof, and is not limited to the system and software described herein.

Figure 2:
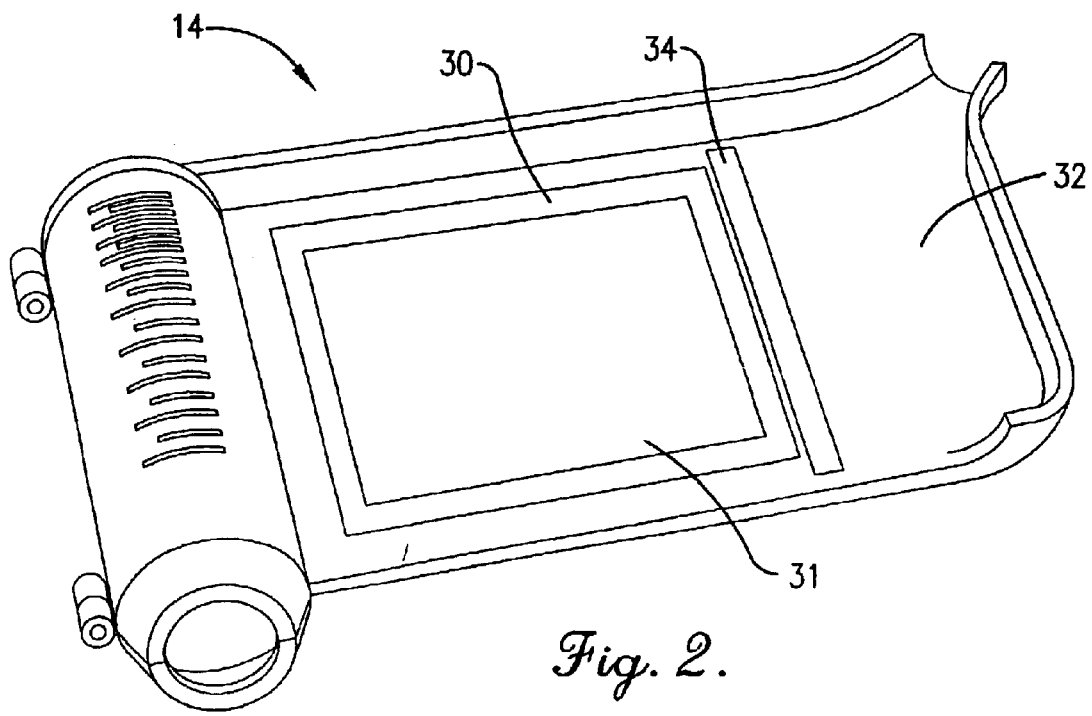
FIG. 2 is a preferred embodiment of a pharmacist's tray shown in FIG. 1 as part of a preferred system.
Figure 3:
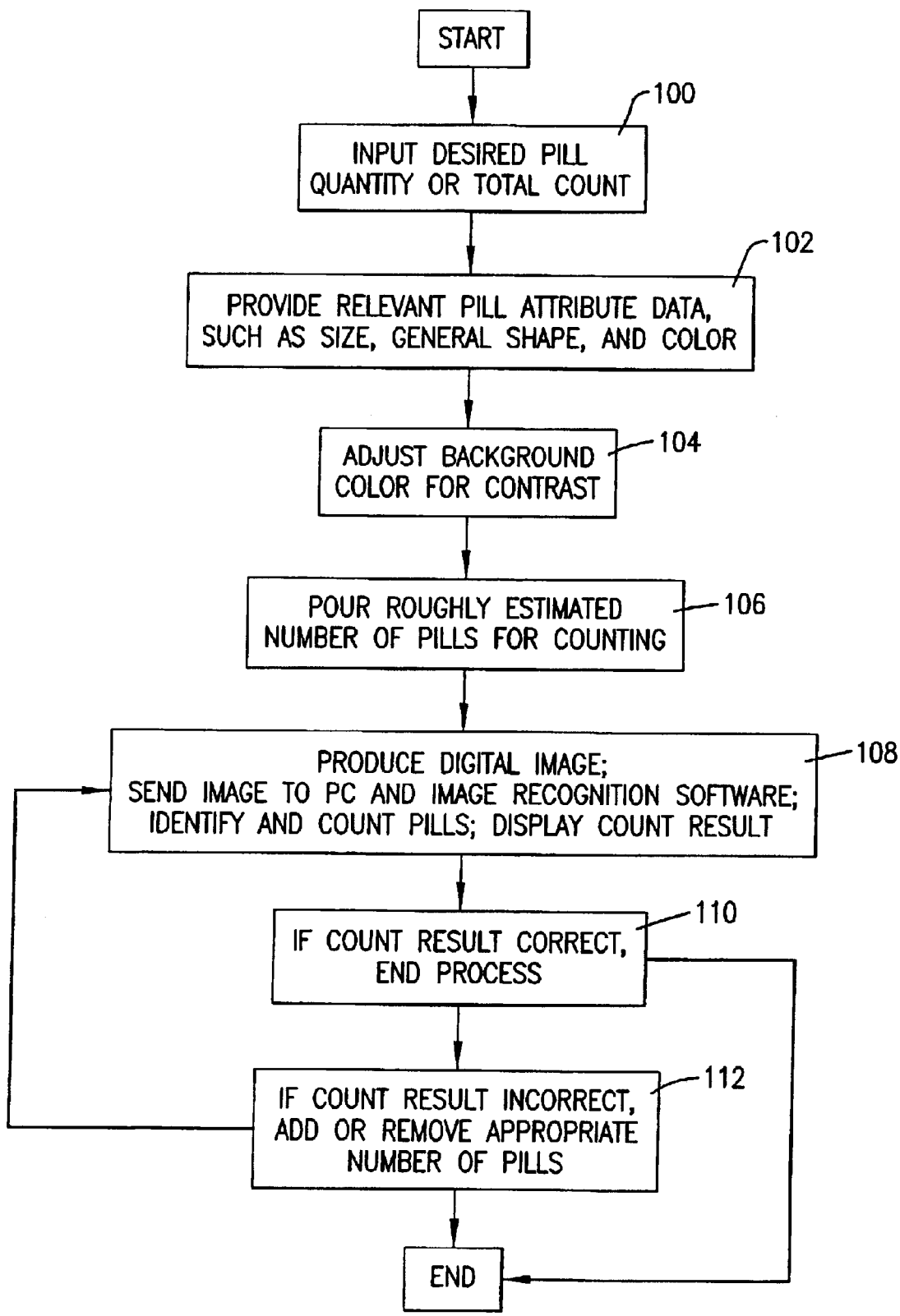
FIG. 3 is a flow diagram showing the steps in a preferred method of practicing the present invention.

The preferred method broadly comprises seven steps, as shown in FIG. 2. Additional steps may be added as desired or needed to adapt the method to particular applications or circumstances without departing from the contemplated scope of the present invention. The method description assumes that the system 10, described above, has been installed and configured correctly.

In step 1, as depicted by box 100, a desired pill quantity or total count is provided to the counting software. This may be accomplished manually, for example, by an operator using a keypad or keyboard or other input device associated with the PC 18. Alternatively, the prescription may be received electronically and stored in a queue, in which case the PC 18 is provided with the count data automatically.

In step 2, as depicted in box 102, pill attribute data is provided to the image recognition software. Relevant pill attributes include size, general shape, and color. Such data may be operator entered using the keypad or keyboard; automatically retrieved, given the pill name, from a pre-existing database; or automatically determined from exposure to a single pill before counting. In a contemplated embodiment, each bulk pill container includes a scannable bar code providing either just the pill name, from which attribute data may be determined, or all relevant attribute data. This latter embodiment, when combined with electronic prescriptions, advantageously allows for automatically verifying that the scanned pill matches the prescribed pill.

In step 3, as depicted in box 104, the background color is adjusted for desirable color contrast. As described above, color adjustment may be accomplished manually by changing colored tray inserts.

In step 4, as depicted in box 106, the operator pours a roughly estimated number of pills upon the first tray portion 30 for counting.

In step 5, as depicted in box 108, the counting process is initiated causing the digital camera 16 to produce a digital image of the pills on the first tray portion 30 and send the image to the PC 18 via the interface 15, where it is received by the image recognition software. The counting algorithm identifies individual pills from the image and counts them. When the count is complete, a count result is communicated by the PC monitor 22 or other display.

In step 6, as depicted in box 110, if the count result does match, the process ends whereafter excess pills are returned to a bulk container and counted pills are bottled, labeled, and dispensed. If, however, as depicted in box 112, the count result does not match the desired quantity, pills are added or removed as required. In this latter case, step 5 may be repeated to confirm that the correct number of pills were added or removed. In some embodiments, the system 10 affects an automatic refresh at a pre-established refresh rate so that step 5 will be automatically periodically repeated until the system 10 is reset or powered down.

In another embodiment, the tray 14 or at least the first portion 30 thereof is transparent and rests on a horizontally-oriented background display (not shown), such as a liquid crystal display or computer monitor, or other surface operable to change color in response to an input or stimulus. In this embodiment, step 3 of the above-described method, which involves background color-contrasting, may be affected automatically or semi-automatically. For example, pill color, being a pill characteristic, may be retrieved, given the pill name, from a pre-existing database, and the background display changed automatically to present a contrasting color.

In this embodiment, it is also contemplated that the image recognition software, having counted the pills present in the digital image and found an excess, be operable to indicate via the background display which pills to remove from the first tray portion 30 to achieve the desired prescription count. This may be accomplished, for example, either with a moveable line boundary between groups of excess and non-excess pills, possibly including different background colors on either side of the line boundary, or individually indicating excess pills for removal, possibly using circles or arrows. Thus, the pharmacist need count no pills whatsoever—he or she need only roughly estimate the number of pills to place upon or add to the tray 14 and remove any excess to the second tray portion 32 as indicated by the background display.

It should be noted that the image recognition and counting software is not limited to identifying and counting a single type of pill per program execution. Rather, different quantities of different types of pills may be identified and counted at the same time. This is particularly important where the pharmacist is engaged in "compliance packaging", which involves single dose packaging of a number of different pills to reduce risks of forgetting to take or having taken a dose of one or more of the pills.

Although the invention has been described with reference to the preferred embodiment illustrated in the attached drawing figures, it is noted that equivalents may be employed and substitutions made herein without departing from the scope of the invention as recited in the claims. Those with skill in the art will appreciate that numerous different embodiments of hardware, software, firmware or combinations thereof exist for practicing the present invention. For example, as noted, the system 10 may be unitized or made portable by reducing component size and power requirements; using dedicated hardware or firmware, such as the disclosed alternate processor and display; combining the components in a single lightweight housing; or affecting other appropriate adaptations. Accordingly, the present invention should not be viewed as limited to the particular illustrative embodiment shown and described.

Furthermore, the invention may be easily adapted to other contexts and applications and is not limited to assisting pharmacists in counting pills. Broadly, the invention has application wherever a number of relatively small items must be quickly and accurately counted and where manual counting and relatively large mechanical counting devices are impractical. For example, a bank or casino may employ the present invention at each teller or dealer station to quickly and accurately count small quantities of coins or chips. In another example, hardware stores may employ the present invention to quickly and accurately count an order or purchase of nuts, bolts, or screws. And note, as described above in the context of compliance packaging, the present invention is able to identify and count different types of coins or chips or nuts, bolts, and screws simultaneously.

Having thus described the preferred embodiment of the invention, what is claimed as new and desired to be protected by Letters Patent includes the following:

What is claimed is:

1. A system for counting a quantity of pills, the system comprising:
   a pharmacist's tray upon which the quantity of pills may be arranged;
   a digital camera operable to produce a digital image of the quantity of pills arranged upon the pharmacist's tray;
   a processor interfaced with the digital camera and operable to receive the digital image, execute a program to count the number of pills present in the digital image, and generate a count result; and
   a display operable to communicate the count result.

2. The system as set forth in claim 1, wherein the program uses an image recognition algorithm based upon a Hough Transform.

3. The system as set forth in claim 2, wherein the Hough Transform is modified in that adjustments of scale are omitted.

4. The system as set forth in claim 1, further comprising a light source operable to illuminate the pharmacist's tray.

5. The system as set forth in claim 1, wherein the pharmacist's tray includes a divided surface on which the pills may be separated into distinct portions.

6. The system as set forth in claim 5, wherein the pharmacist's tray further includes a small motor for vibrating the tray to ensure even, single-layer distribution of the pills to be counted.

7. The system as set forth in claim 1, wherein the pharmacist's tray presents a background surface having a changeable color.

8. The system as set forth in claim 7, wherein removable colored inserts are used to change the changeable color of the background surface.

9. A system for counting a quantity of pills, the system comprising:
   a pharmacist's tray upon which the quantity of pills may be arranged, wherein the pharmacist's tray has a first end and a second end and includes a divided surface, wherein the first end includes a hinged covered portion, and the second end includes a tapered spout through which the pills may be funneled into a vial;
   a digital camera operable to produce a digital image of the quantity of pills arranged upon the phammcist's tray;
   a processor interfaced with the digital camera and operable to receive the digital image, execute a program to count the number of pills present in the digital image, and generate a count result; and
   a display operable to communicate the count result.

10. The system as set forth in claim 9, wherein the program uses an image recognition algorithm based upon a Hough Transform.

11. The system as set forth in claim 10, wherein the Hough Transform is modified in that adjustments of scale are omitted.

12. The system as set forth in claim 9, wherein the phamiacist's tray further includes an anti-reflective surface to avoid image interference.

13. The system as set forth in claim 9, wherein the pharmacist's tray further includes a mechanism for vibrating the tray to ensure single-layer distribution of the pills.

14. A method of counting pills, the pills having one or more visually identifying characteristics, the method comprising:

(a) receiving a desired quantity input of pills, wherein the pills are arranged on a pharmacist's tray for counting;

(b) producing a digital image of the pills;

(c) identifying and counting the pills present in the digital image based upon the visually identifying characteristics;

(d) generating a count result; and (e) displaying the count result.

15. The method as set forth in claim 14, further comprising the step of (f) adjusting a background color of the pharmacist's tray based upon a pill color.

16. The method as set forth in claim 14, further comprising the step of (f) displaying a number equal to a difference between the desired quantity input and the count result.

17. The method as set forth in claim 14, further comprising the step of (f) indicating, when the count result exceeds the desired quantity input, pills whose removal, based upon the digital image, would cause the count result to equal the desired quantity input.

* * * * *